United States Patent [19]
Mullen

[11] Patent Number: 5,824,337
[45] Date of Patent: Oct. 20, 1998

[54] SYNTHETIC MEMBRANES FORMING MICELLES AND MICELLE-LIKE STRUCTURES COMPRISING LIPO-GLYCOPROTEIN MEMBRANES

[76] Inventor: Elaine Mullen, 6733 W. Wakefield Dr., B2, Alexandria, Va. 22307

[21] Appl. No.: 621,611

[22] Filed: Mar. 26, 1996

Related U.S. Application Data

[63] Continuation-in-part of Ser. No. 280,520, Jul. 26, 1994.

[51] Int. Cl.⁶ .......................... A61K 9/127; A61K 9/107
[52] U.S. Cl. ........................... 424/450; 264/41; 514/937
[58] Field of Search ................... 424/450; 514/936–943; 264/4.1

[56] References Cited

U.S. PATENT DOCUMENTS

| | | | |
|---|---|---|---|
| 4,790,987 | 12/1988 | Campass | 424/89 |
| 5,071,964 | 12/1991 | Dustin | 530/395 |

*Primary Examiner*—Gollamudi S. Kishore, PhD
*Attorney, Agent, or Firm*—Glenna Hendricks

[57] ABSTRACT

Micelles are produced having a membrane wherein the outer surface is hydrophilic and the interior of said micelle contains at least one lipophilic group. If a lipophilic material will not form strong micelles, it is possible, using methods of the invention, to provide stronger micelles by use of two lipophilic materials. These micelles have a glycoprotein layer on the outside with a double layer of lipid wherein the first lipid forms a membrane with the glycoprotein and the second lipid is within the membrane.

11 Claims, No Drawings

SYNTHETIC MEMBRANES FORMING MICELLES AND MICELLE-LIKE STRUCTURES COMPRISING LIPOGLYCOPROTEIN MEMBRANES

This application is a continuation-in-part of U.S. Ser. No. 08/280,520, filed Jul. 26, 1994, now pending in an action before the Board of Appeals.

FIELD OF THE INVENTION

This invention relates to the field of membranes containing both hydrophobic and hydrophilic groups. Such structures include micelles and liposomes. The membranes of the invention are particularly useful for protection of substances which are lipids or lipophilic or are soluble or easily dispersed in organic solvents. The structures of the invention can be used to protect volatile substances from dispersal into the immediate environment. The structures of the invention also provide means for protecting substances contained within the hydrophobic compartment from reaction or degradation until the structures are disrupted. Because the structures are relatively stable in aqueous media, they can be used to hold or transport non-polar lipids and lipophilic substances in aqueous environments. By methods of the invention, it is possible to isolate glycoproteins by forming micelles with volatile hydrocarbons.

BACKGROUND OF THE INVENTION

Micelles are aggregates of substances in which hydrophilic polar groups of compounds orient themselves toward and interact with the aqueous phase and their hydrophobic nonpolar hydrocarbon chains are hidden within the structure. For example, micelles which contain soap molecules remain evenly suspended in water because their surfaces are negatively charged and the micelles repel each other. Micelles prepared from phospholipids and oligosaccharide-lipid complexes have been used in preparation of vaccines using natural and synthesized oligosaccharides which are immunogens to provide stabilized vaccines. See U.S. Pat. No. 5,034,519, which is incorporated herein by reference. Preparation of micelles and liposomes from phospholipids is known. For example, micelle-forming amphiphiles include lysophospholipid, gangliosides, sulfatide, synthetic glycopholipids and lipophilic drugs such as cytosine arabinoside. See, for example, U.S. Pat. No. 5,043,164, which is incorporated herein by reference. It is also known that amphipathic proteins such as cytochrome oxidase, an intrinsic enzyme found in mitochondrial membranes, when placed in a suspension with lipids, form sac-like vesicles that are, in effect, man-made membranes. Such vesicles have been used as model systems for the study of the isolated protein's relationship with lipid bilayers. U.S. Pat. No. 4,790,987 to Compans (which is incorporated herein in its entirety) teaches the preparation of viral glycoprotein subunit vaccine by complexing a lipid with the glycoprotein. That reference teaches that the such complexes can be obtained by dissolving a lipid in a dialyzable detergent solution containing glycoprotein, then dialyzing the solution to obtain the protein-lipid complex. The lipids suggested are phospholipids. The resulting complexes are then administered in pharmaceutically acceptable carriers.

SUMMARY OF THE INVENTION

Micelles are produced having a membrane wherein the outer surface is hydrophilic and the interior of said micelle contains at least one lipophilic group. The micelles are prepared by (1) layering a lipid on top of an aqueous mixture containing at least one glycoprotein, (2) allowing a membrane to form at the lipid/aqueous interface, and (3) agitating the composition obtained in step (2) until micelles are formed. The micelles may be made smaller by repeated passage through a screen or by pouring repeatedly from one container into another. The micelles of the invention do not usually adhere to one another while in the aqueous mixture.

It is also possible to produce micelles containing a second lipid or lipophilic material wherein the second material is of such a nature that it will not, alone, form strong micelles using the method described above. The second method requires (1) introducing a small amount of an aqueous solution containing glycoprotein into a non-polar compound or composition such as a lipid in very small increments whilst agitating the mixture until an emulsion is formed. After the emulsion is formed (3) adding a small amount of a second lipid slowly to the composition and shaking and (4) then adding a large amount of glycoprotein-containing solution to the composition and shaking until stable micelles are formed. These micelles have a glycoprotein layer on the outside with a double layer of lipid wherein the first lipid forms a membrane with the glycoprotein and the second lipid is within the membrane.

DETAILED DESCRIPTION OF THE INVENTION

It is the purpose of this invention to provide economical micelles and micelle-like structures which can be used as carriers for protection of substances which are lipids or lipophilic or are soluble or easily dispersed in oils or other lipid-like compounds. Examples of such substances include drugs which are lipophilic such as immunogens or steroids, fragrances, flavorings and nutrients. For industrial use, the constructs of the invention may be useful for protection of gases, dyes and other coloring agents and catalysts. Furthermore, a reactant can be protected from a co-reactant in the solution environment until interaction is desired. The constructs of the invention are useful for delivering to an organism materials which might deteriorate before ingestion. By use of the inventive structures, it is possible to administer substances in foods which might, when not protected, add an unpleasant flavor or odor to foods. Unlike previously described micelles the constructs of the instant invention need not contain lipids with phosphate moieties.

It is a second purpose to provide micelles containing more than one lipid, lipophilic, or lipid-like substance. By this method it is possible to provide micelles which are relatively stable and which act as carriers for substances that are not, when used alone, capable of forming relatively stable micelles. For example, it is possible, using the methods of the invention, to enclose diallyl sulfide, the odorous compound found in garlic, within micelles so that the disulfide can be neither tasted nor smelled when the micelles are ingested. Similarly, flax seed oil, which often has a disagreeable odor and taste, can be incorporated into micelles and ingested.

Glycoproteins used in the method of the invention can vary in form and source. It has now been found that glycoproteins will associate with lipids and lipid-like substances when even they are mixed with distilled water in dilute solution. (Many of the glycoproteins are fragile, and will precipitate in tap water or basic solutions. Hence, distilled water is preferred for making micelles.) Glycoproteins associate with the lipids floating on the surface to form a flexible membrane-like structure at the interface. The membrane-like structure, when rolled or shaken, will break into micelles filled with oil. The polar surfaces exposed to the aqueous solution do not fuse easily and are stable in aqueous solution. The smaller micelles will eventually rise in the solution, but may, for several minutes to several hours, be selectively extracted by usual methods such as by separatory funnel or by syringe. Hence, it is possible to obtain micelles of relatively uniform size.

In fabrication of lipo-glycoprotein micelles having a hydrophilic outer surface, the lipid is layered onto a solution containing the glycoprotein(s). Conversely, if the glycoproteins are poured in small amounts into the lipids, the resulting membrane has a hydrophobic outer surface. In the latter case, the micelles will fuse easily. Micelles of the invention may be made using easily available glycoproteins such as water-soluble portion of egg white. Micelles having the hydrophilic surface exposed may be very resistant to destruction. The micelles can be disrupted by heat, desiccation or proteases in basic solution. The surface tension of the micelle is influenced by several factors including the relative temperature of the lipid and glycoprotein-containing phases during fabrication of the micelles, the concentration and type of glycoprotein and particular lipid(s) used, and the size of container in which fabrication occurs. Hence, it is possible to control both the size and the fragility of the micelles. It is also possible to form the micelles using juice from vegetables and fruits which contain glycoproteins. Juice from onions, oranges and grapefruit are exemplified herein. However, these examples should not be considered as limitations to the teachings. It should be remembered, however, that many forces such as heating and exposure to enzymes denature glycoproteins. Surprisingly, many of the micelles of the invention are resilient and often mend spontaneously when broken by heat or mechanical deformation.

Many of the structures of the invention may be stored in a variety of environmental conditions for extended periods of time. Many of the micelles are stable when transferred from one aqueous medium to another. Micelles which have been dried may be fragile, but can often be rehydrated. The ability of micelles to retain their shape and hold their contents varies with the particular glycoprotein and lipids used for their preparation. Glycoproteins are antigens and can give rise to immune responses. It would be possible to make micelles carrying desirable therapeutic properties using glycoproteins from tissue of the individual who is to receive the therapeutic agent. In some instances, glycoprotein used may be obtained from the target tissue.

Micelles of the invention having diameter as small as about $0.1\mu$ may be made by passing the suspension containing the micelles through the appropriate size mesh. Nylon mesh of with openings of about $100\mu$ made with single strands have been shown to be particularly useful. Smaller micelles may be obtained by multiple passages through the mesh and/or by increasing the pressure under which the liquid containing the micelles is forced through the mesh. Use of mesh made with metallic materials is not advised, since oligosaccharides are reducing sugars and the use of metallic materials may result in absorption of metallic residues.

After the membrane is formed at the interface between the aqueous and lipid phase, water dropped on the membrane will drop through the lipid layer and membrane and enter the aqueous phase below the membrane. The membrane will then mend the opening made by the water droplet. However, an aqueous solution of glycoprotein placed on the oil will sink into the oil phase and will form a second membrane. Fluid above the double membrane will, by virtue of its weight relative to oil, be suspended by the membrane down into the aqueous solution.

Once the micelles having hydrophilic outer surfaces have been produced, they can be washed and can then be resuspended in a variety of fluids. It is, therefore, possible to make micelles in one liquid, then add them to another. By means disclosed herein, it is possible to introduce the micelles into foods such as juices and candies to provide desired nutrients. For example, diallyldisulfide is believed to have anti-cancerogenic properties. However, because of the strong odor and taste, administration of this compound has proven to be difficult. It is now possible, using the methods of the invention, to make micelles containing garlic oil rich in diallyl-disulfide using the glycoproteins found in oranges.

Natural glycoproteins which have been used in the processes of the invention include those obtained from such widely diverse sources as tissue fluid from chicken skin, non-fat milk, orange juice, grapefruit juice and onion juice.

While oils such as olive oil, peanut oil, corn oil, canola oil, and linseed oil have been used, it has also been possible to prepare micelles using hexane. If a fine emulsion has been prepared in oil which comprises the lipid phase, the micelles will contain, in the lipid fraction, polar molecules present in the emulsion immediately after formation. With time, the polar molecules tend to be released from the interior of the micelle.

The following examples are meant to exemplify various embodiments of the invention, and are not meant to fully define the invention.

EXAMPLE 1

Tumeric was placed in olive oil over night. The yellowish-colored oil was decanted from the mixture. The decanted, yellowish oil was layered on top of the water-soluble portion of cold egg white and swirled. Ovoid micelles were formed. Non-chlorinated water was added to the mixture and the micelles were lifted from the surface of the resulting mixture.

The micelles were studied microscopically. Micelles having a wrinkled membrane which contained a yellowish material were seen.

EXAMPLE 2

Fresh mint leaves were ground in olive oil. The oil was poured over the water-soluble portion of egg white. The mixture was gently shaken from side to side until all of the oil was seen to be contained in large membrane-bound vesicles. The entire mixture was then poured through a nylon screen. The leaf debris was retained by the screen. The filtrate containing small, oil-filled micelles was poured into water, then repeatedly passed through a nylon screen until small micelles of about $5\mu$–$30\mu$ were obtained.

The mixture of micelles in water was placed in narrow-mouthed open bottles and allowed to rest over night. In the morning, all of the micelles had collected at the top of the bottle. No odor of mint could be detected at the mouth of the bottle. The micelles were then removed from the bottle and subjected to pressure. The odor of mint was then detected.

EXAMPLE 3

Chicken skin was removed from the breast of a chicken and allowed to stand in a cup of distilled water for about 10 minutes. The water containing tissue fluid which had been extracted from the skin was decanted. Olive oil was layered on top of the water containing tissue fluid. After about 10 minutes a delicate membrane could be seen forming at the water/oil interface. Upon shaking small, irregularly shaped micelles were formed. The micelles persisted for about an hour, after which they were discarded.

EXAMPLE 4

The water-soluble portion of egg white is mixed in an equal portion of distilled water. A composition is prepared by mixing 5000 units of Vitamin $D_2$ and 5 ml of sesame oil. The sesame oil/Vitamin D mixture is layered on top of 25 ml of the dilute egg white in a separatory funnel. After a membrane is formed and precipitated proteins have settled, the debris in the lower portion of the funnel is removed and discarded. Water is added and vessel is shaken until micelles are formed. The mixture is poured 4× through a single stranded nylon screen. Large micelles are allowed to rise to the top of the composition. Micelles are then separated by size.

EXAMPLE 5

Preparations of micelles using olive oil and, in the second instance, peanut oil, were compared. In each instance, the oil was layered on the water-soluble portion of egg white. In each instance distilled water was added after the membrane was formed at the interface. The resulting compositions were shaken and the micelles formed were removed and examined microscopically. Micelles formed from the peanut oil were more round and resistant to breaking into smaller units than those made from olive oil.

EXAMPLE 6

Preparation of Micelles Having the Oil Layer on the Outside:

Freshly-squeezed orange juice (about ½ tablespoon) was added drop-wise to peanut oil (about 1 ½ tablespoon) with constant agitation until an emulsion formed. After the emulsion had formed, about ⅓ tsp. of garlic oil which had a strong odor (obtained from capsules) was added with shaking to the emulsion.

Inversion of the Micelles:

Freshly squeezed orange juice was added to the emulsion and shaken until the emulsion was replaced with micelles and all odor from the garlic oil had disappeared. The orange juice containing the micelles neither smelled or tasted of garlic.

Some of the micelles were added to jellied candy which had been softened and partially liquified. The candy was then allowed to cool. When cooled, the candy was offered to persons who did not know the candy contained any unusual ingredient. Neither person could detect any unusual flavor in the candy.

EXAMPLE 7

The method of example 6 was followed, the only difference being that the garlic oil was replaced with flax seed oil. Again, the flax seed oil could not be tasted or smelled.

The micelles of the invention may also be used advantageously as carriers of lipophilic, lipid or lipid-like odorants. For example, odorants such as those used to train animals to detect humans and certain contraband cause nausea and discomfort to those required to apply such odorants to objects, since the odor emitting from containers of such odorants is very strong. Micelles made in accord with the teaching of this disclosure may be shipped in solutions, then applied to objects. The micelles can be subjected to agitation to release the odorants on the objects to which the micelles have been applied.

The instant invention also makes it possible to selectively isolate glycoprotein from a solution of proteins and glycoproteins without the use of lipids containing phosphate or sulfate groups and without the use of detergents. Micelles are prepared in accord with the teachings of this specification. However, the novel process, unlike the process of Compans, does not require the use of either detergents or phospholipids. By varying the relative amount of lipid or lipid-like material and glycoprotein, it is possible to selectively obtain micelles with the glycoprotein on the inner or outer layer of the micelles. In other words, one may prepare vesicles wherein the glycoprotein is on the outer surface of the micelle and with a lipid occupying the interior of the micelle, or the vesicles may be prepared in such a manner that the glycoprotein is inside the micelle and the lipid layer is on the outer surface of the micelle, as is exemplified in Example 6 in the first step. In the latter case, the micelles are unstable in aqueous solution.

Attempts were made to disrupt the micelles having the glycoprotein exterior. Many of the micelles were impervious to addition of acid or base. However, in the presence of base and protease, the micelles ruptured. The environment of the small intestine provides high pH along with proteases. Hence, the environment of the small intestine would cause these micelles to release their contents. Hence, the micelles of the invention having a glycoprotein exterior provide a means of delivery of many active agents such as linolenic acid and diallyl disulfide to the small intestine.

I claim:

1. A method of producing a micelle comprising the steps of:
    (1) slowly introducing a small amount of a polar solution containing glycoprotein in an amount sufficient to form an emulsion into a non-polar composition with agitation until an emulsion is formed;
    (2) adding to the emulsion formed in step (1) a third composition containing at least one lipid or lipophilic agent with the proviso that said third composition contains a lipid or lipophilic agent which is not the same as the non-polar material used in step (1) and agitating; and
    (3) adding to the composition formed in step (2) a polar solvent which may, additionally, contain glycoprotein and agitating until micelles are formed.

2. A method of claim 1 wherein the nonpolar composition used in step (1) is an oil.

3. A method of claim 1 wherein the lipid added to the emulsion in step (2) contains diallyl disulfide.

4. A method of claim 1 wherein, in step (2), a composition containing a lipophilic dye or pigment is added.

5. A method of claim 1 wherein, in step (2), a composition containing a vitamin is added.

6. A method of making a micelle wherein the outer surface is hydrophilic and the interior of said micelle contains at least one lipid comprising the steps of:
    (1) layering a lipid on top of an aqueous solution containing at least one glycoprotein,
    (2) allowing a membrane to form at the lipid/aqueous interface, and
    (3) agitating the composition obtained in step (2) to break up the membrane and form micelles.

7. A method of claim 1 wherein the composition added in step (2) is odorous.

8. A method of claim 1 wherein the composition added in step (2) is a nutrient.

9. A method of claim 8 wherein the composition added in step (2) is garlic oil.

10. A method of claim 8 wherein the composition added in step (2) contains linolenic acid.

11. A method of claim 1 wherein the composition added in step (2) contains a flavoring.

* * * * *